(12) United States Patent
Mashak

(10) Patent No.: US 8,479,733 B2
(45) Date of Patent: Jul. 9, 2013

(54) SYSTEM AND METHOD FOR A FLOW SENSOR

(75) Inventor: James Nyal Mashak, Sun Prairie, WI (US)

(73) Assignee: General Electric Company, Schenectady, NY (US)

( * ) Notice: Subject to any disclaimer, the term of this patent is extended or adjusted under 35 U.S.C. 154(b) by 676 days.

(21) Appl. No.: 12/360,505

(22) Filed: Jan. 27, 2009

(65) Prior Publication Data

US 2010/0186745 A1 Jul. 29, 2010

(51) Int. Cl.
*A62B 9/02* (2006.01)
*G01F 1/37* (2006.01)

(52) U.S. Cl.
USPC ............... 128/205.24; 73/861.53; 73/861.52

(58) Field of Classification Search
USPC ...... 73/861.53, 861.52; 137/855; 128/204.26, 128/205.24, 200.24, 200.26, 204.22, 202.28, 128/203.11
See application file for complete search history.

(56) References Cited

U.S. PATENT DOCUMENTS

| | | | | |
|---|---|---|---|---|
| 3,354,903 A | * | 11/1967 | Caruso | 137/512.15 |
| 4,083,245 A | * | 4/1978 | Osborn | 73/861.53 |
| 4,838,262 A | * | 6/1989 | Katz | 128/205.24 |
| 4,993,269 A | * | 2/1991 | Guillaume et al. | 73/861.53 |
| 5,038,621 A | | 8/1991 | Stupecky | |
| 5,137,026 A | * | 8/1992 | Waterson et al. | 600/538 |
| 5,405,269 A | | 4/1995 | Stupecky | |
| 5,860,449 A | * | 1/1999 | Schulte | 137/550 |
| 5,970,801 A | * | 10/1999 | Ciobanu et al. | 73/861.52 |
| 6,119,723 A | * | 9/2000 | Kenyon | 137/527 |
| 6,648,004 B2 | * | 11/2003 | Lau | 137/223 |
| 6,830,074 B2 | * | 12/2004 | Wang | 137/855 |
| 6,915,705 B1 | * | 7/2005 | Truitt et al. | 73/861.52 |
| 7,331,360 B2 | * | 2/2008 | Camis, Jr. | 137/512.3 |

OTHER PUBLICATIONS

Applicant's Statement (attached).
Office Action issued by State Intellectual Property Office, PR China for corresponding Chinese Patent Appln. No. 201010115742.0 dated Jul. 13, 2012.

* cited by examiner

*Primary Examiner* — Elizabeth Houston
*Assistant Examiner* — Bradley Philips
(74) *Attorney, Agent, or Firm* — Andrus Sceales Starke & Sawall, LLP

(57) ABSTRACT

A flow sensor for a medical ventilator system is disclosed herein. The flow sensor includes a valve assembly having a valve seat, and a valve flap attached to the valve seat. The valve flap is composed of an elastomeric material configured to generate a pre-load that biases the valve flap into engagement with the valve seat such that the valve assembly remains closed in the absence of an externally applied force. The flow sensor also includes a pressure transducer configure to measure a first pressure level at an upstream position relative to the valve assembly, and a second pressure level at a downstream position relative the valve assembly. The flow sensor also includes a processor configured to estimate the flow rate of a fluid passing through a medical ventilator system based on the first and second pressure levels.

17 Claims, 6 Drawing Sheets

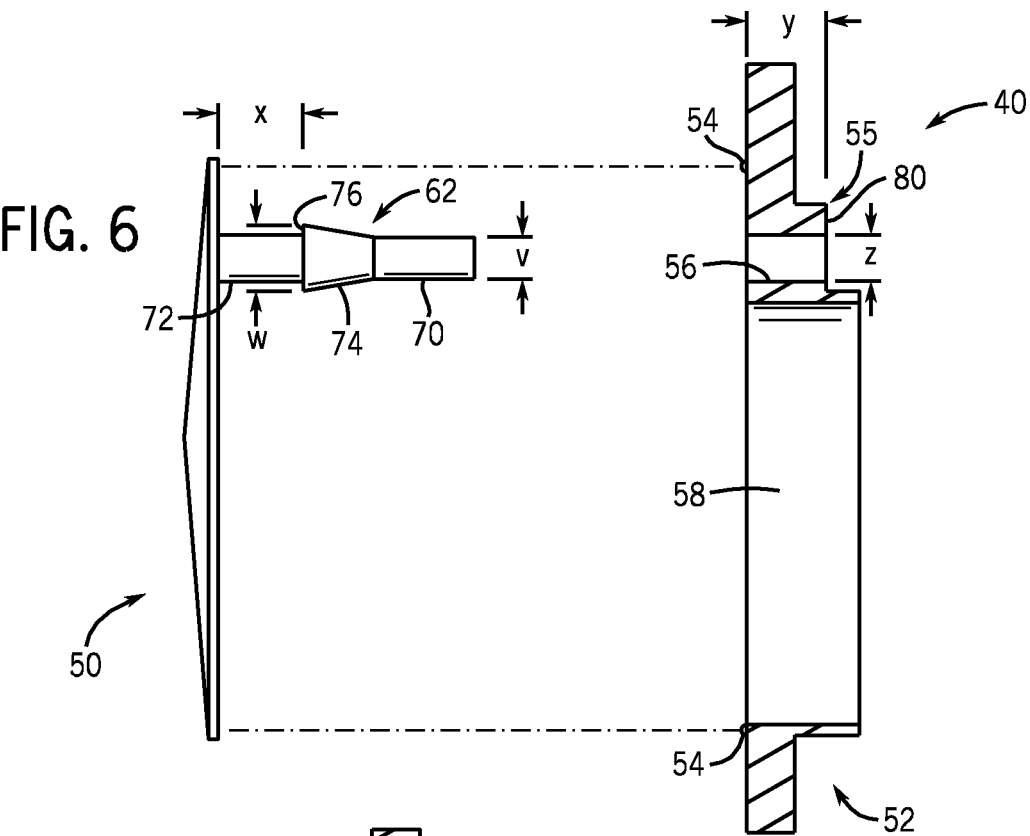
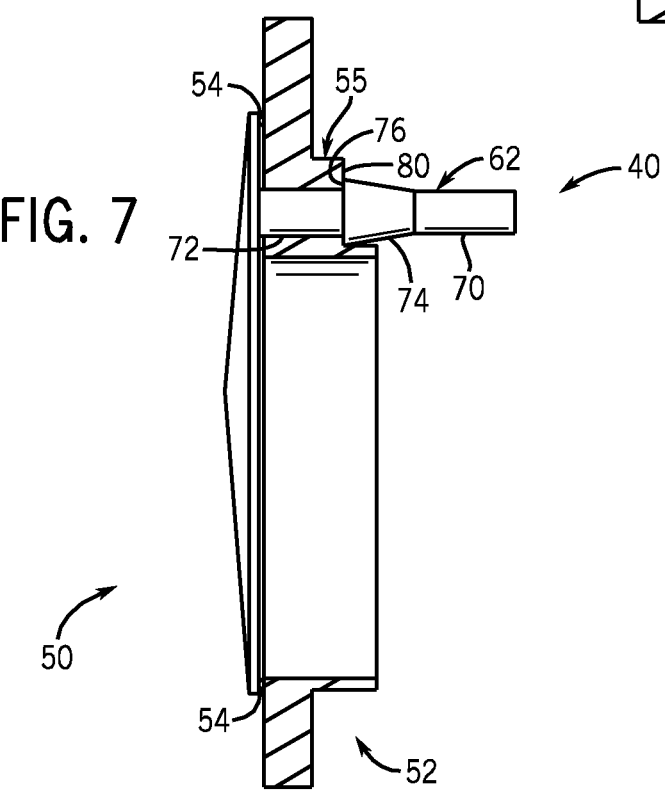

SYSTEM AND METHOD FOR A FLOW SENSOR

FIELD OF THE INVENTION

This disclosure relates generally to system and method for a flow sensor that may be implemented in a medical ventilator system.

BACKGROUND OF THE INVENTION

Medical ventilator systems are used to provide respiratory support to patients undergoing anesthesia and respiratory treatment whenever the patient's ability to breath is compromised. The primary function of the medical ventilator is to maintain suitable pressure and flow of gases inspired and expired by the patient. Medical ventilator operation is commonly regulated based on feedback from one or more flow sensors. The flow sensors are generally disposed within or otherwise pneumatically coupled with a breathing circuit. One problem with conventional ventilator systems is that such systems require accurate and reliable flow sensors that are expensive to manufacture.

BRIEF DESCRIPTION OF THE INVENTION

The above-mentioned shortcomings, disadvantages and problems are addressed herein which will be understood by reading and understanding the following specification.

In an embodiment, a flow sensor for a medical ventilator system includes a valve assembly. The valve assembly includes a valve seat, and a valve flap attached to the valve seat. The valve flap is composed of an elastomeric material. The elastomeric material of the valve flap is configured to generate a pre-load that biases the valve flap into engagement with the valve seat such that the valve assembly remains closed in the absence of an externally applied force. The flow sensor also includes a pressure transducer configure to measure a first pressure level at an upstream position relative to the valve assembly, and a second pressure level at a downstream position relative the valve assembly. The flow sensor also includes a processor connected to the pressure transducer. The processor is configured to estimate the flow rate of a fluid passing through a medical ventilator system based on the first and second pressure levels.

In another embodiment, a medical ventilator system includes a ventilator, a breathing circuit pneumatically coupled with the ventilator, and a flow sensor pneumatically coupled with the breathing circuit. The flow sensor includes a valve assembly comprising a valve seat, and a valve flap composed of an elastomeric material. The valve flap comprises a protrusion configured to retain the valve flap to the valve seat. The valve flap protrusion is elastically deformed during the process of attaching the valve flap to the valve seat. The elastic deformation of the valve flap protrusion generates a pre-load that biases the valve flap into engagement with the valve seat such that the valve assembly remains closed in the absence of an externally applied force. The medical ventilator system also includes a pressure transducer configure to measure a first pressure level at an upstream position relative to the valve assembly, and a second pressure level at a downstream position relative the valve assembly. The medical ventilator system also includes a processor connected to the pressure transducer. The processor is configured to estimate the flow rate of a fluid passing through the medical ventilator system based on the first and second pressure levels.

In another embodiment, a method for estimating a flow rate of a fluid passing through a medical ventilator system includes providing a breathing circuit, providing a valve assembly comprising providing a valve flap composed of an elastomeric material, and assembling the valve flap to a valve seat such that the elastomeric material of the valve flap is elastically deformed during the assembly process. The elastic deformation generates a pre-load that biases the valve flap into engagement with the valve seat such that the valve assembly remains closed in the absence of an externally applied force. The method for estimating a flow rate of a fluid passing through a medical ventilator system also includes estimating a first pressure level within the breathing circuit at an upstream position relative to the valve assembly. The method for estimating a flow rate of a fluid passing through a medical ventilator system also includes estimating a second pressure level within the breathing circuit at a downstream position relative to the valve assembly. The method for estimating a flow rate of a fluid passing through a medical ventilator system also includes estimating a flow rate of a fluid passing through the breathing circuit based on the first and second pressure levels.

Various other features, objects, and advantages of the invention will be made apparent to those skilled in the art from the accompanying drawings and detailed description thereof.

BRIEF DESCRIPTION OF THE DRAWINGS

FIG. 6 is an exploded sectional view illustrating the valve assembly of FIG. 3 in accordance with an embodiment;

FIG. 7 is a sectional view illustrating the valve assembly of FIG. 3 in accordance with an embodiment.

DETAILED DESCRIPTION OF THE INVENTION

In the following detailed description, reference is made to the accompanying drawings that form a part hereof, and in which is shown by way of illustration specific embodiments that may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken as limiting the scope of the invention.

Figure 1:
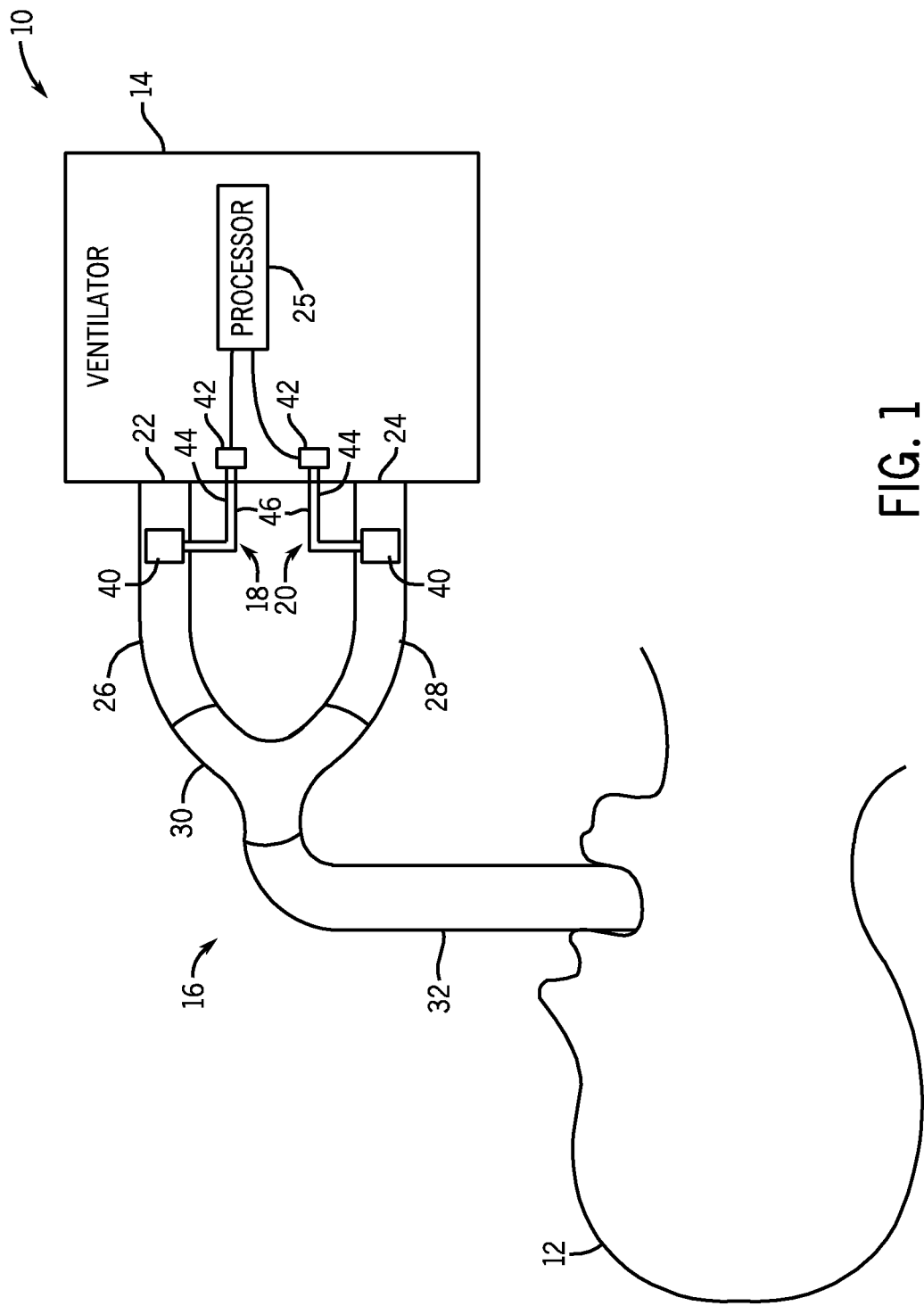
FIG. 1 is a schematic diagram illustrating a ventilator system connected to a patient in accordance with an embodiment.

Referring to FIG. 1, a schematically illustrated ventilator system 10 is shown connected to a patient 12 in accordance with an embodiment. The ventilator system 10 includes a ventilator 14, a breathing circuit 16, an inspiratory flow sensor 18, and an expiratory flow sensor 20. The ventilator 14 includes an inspiratory connector 22, an expiratory connector 24, and a processor 25. The breathing circuit 16 includes an inspiratory branch 26, an expiratory branch 28, a Y-connector 30, and a patient branch 32.

The ventilator 14 is adapted to deliver breathing gasses to the patient 12. The ventilator connectors 22, 24 respectively receive the inspiratory branch 26 and the expiratory branch 28, and thereby pneumatically couple the ventilator 14 with the breathing circuit 16. The ventilator processor 25 is operatively connected to and configured to receive data from the flow sensors 18, 20. According to one embodiment, the data from the flow sensors 18, 20 can be implemented by the processor 25 to provide feedback on the status of the patient 12 and to facilitate ventilator 14 operation.

According to the embodiment depicted in FIG. 1, the ventilator system 10 implements the ventilator processor 25 to convert pressure data from the flow sensors 18, 20 into flow rate data. Alternatively, the flow sensors 18, 20 may individually comprise a separate processor (not shown) configured to provide similar flow rate data in accordance with a slightly different embodiment. The inspiratory flow sensor 18 is configured to estimate the flow rate of inspiratory gasses passing through the inspiratory branch 26 of the breathing circuit 16, and the expiratory flow sensor 20 is configured to estimate the flow rate of expiratory gasses passing through the expiratory branch 28 of the breathing circuit 16. The flow sensors 18, 20 may be operatively connected to or disposed within the breathing circuit 16 as shown in FIG. 1 and described in detail hereinafter. Alternatively, the flow sensors 18, 20 may be incorporated into the ventilator 14 and positioned so they remain in pneumatic communication with the breathing circuit 16.

The flow sensor 18 will now be described in more detail with the understanding that that the flow sensor 20 is generally identical. The flow sensor 18 includes a valve assembly 40 that is pneumatically coupled with a remotely located pressure transducer 42 via a high-pressure tube 44 and a low-pressure tube 46. The pressure transducer 42 is operatively connected to the ventilator processor 25. According to one embodiment, the valve assembly 40 is disposed within the inspiratory branch 26 of the breathing circuit 16, and the pressure transducer 42 is disposed within the ventilator 14.

Figure 2:
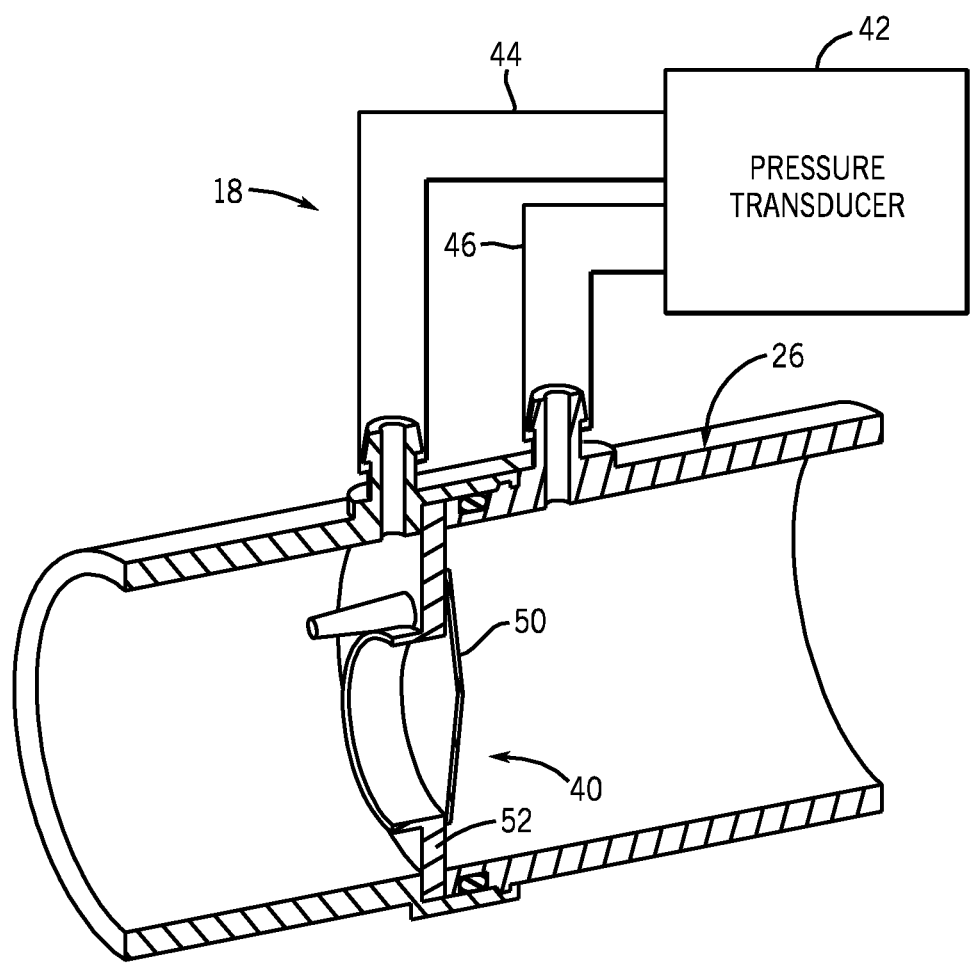
FIG. 2 is a sectional isometric view illustrating a flow sensor valve assembly in the closed position in accordance with an embodiment.

Referring now to FIG. 2, a sectional isometric view illustrates the flow sensor 18 partially disposed within the inspiratory branch 26 of the breathing circuit 16 (shown in FIG. 1) in accordance with an embodiment. FIG. 2 depicts the valve assembly 40 in its closed position. For purposes of this disclosure, the term fluid is defined as a substance that continually deforms or flows under an applied shear stress, and therefore includes both liquids and gases.

According to the depicted embodiment, the valve assembly 40 includes a disc shape valve flap 50 that is pivotally connected to an annular valve seat 52. The high-pressure tube 44 is pneumatically coupled with the inspiratory branch 26 on the upstream side of the valve assembly 40, and the low-pressure tube 46 is pneumatically coupled with the inspiratory branch 26 on the downstream side of the valve assembly 40. The pressure transducer 42 monitors the pressure differential between the pressure level in the high-pressure tube 44 and the pressure level in the low-pressure tube 46. The flow rate of a fluid passing through the valve assembly 40 is proportional to this pressure differential and can be calculated by the ventilator processor 25 (shown in FIG. 1) in a known manner.

In the absence of an externally applied force (e.g., patient inspiration), the periphery of the valve flap 50 engages the annular valve seat 52 to form a circumferential seal and thereby close the valve assembly 40. When the valve assembly 40 is closed, the pressure within the high-pressure tube 44 is generally identical to that within the low-pressure tube 46 such that the pressure differential measured by the pressure transducer 42 is zero. Accordingly, a zero pressure differential as measured by the pressure transducer 42 is indicative of zero flow rate through the inspiratory branch 26.

Figure 3:
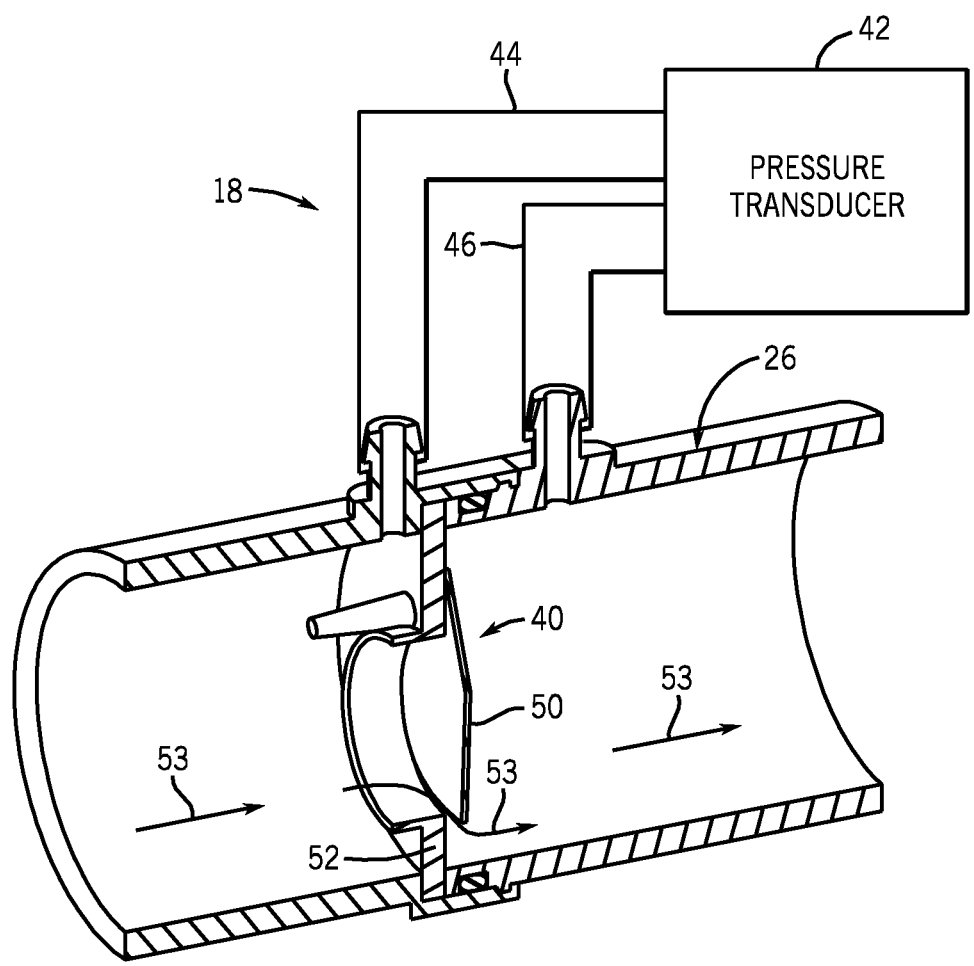
FIG. 3 is a sectional isometric view illustrating a flow sensor valve assembly in the open position in accordance with an embodiment.

When the patient 12 inhales or receives a breathing gas from the ventilator 14 (shown in FIG. 1), a force is exerted upon the valve flap 50 which tends to pivot the valve flap 50 away from the valve seat 52 such that valve assembly 40 opens. Referring to FIG. 3, valve assembly 40 is depicted in its open position which allows the transfer of fluid through the inspiratory branch 26. The arrows 53 represent inspiratory gasses passing through the open valve assembly 40 and through the inspiratory branch 26. It should be appreciated that the process of pivotably opening the valve assembly 40 in response to the forces generated by patient inhalation has the effect of impeding inspiratory flow. This inspiratory flow impediment generates a pressure differential across the valve assembly 40 that can be measured by the pressure transducer 42 and implemented by the ventilator processor 25 to estimate flow rate.

Figure 4:
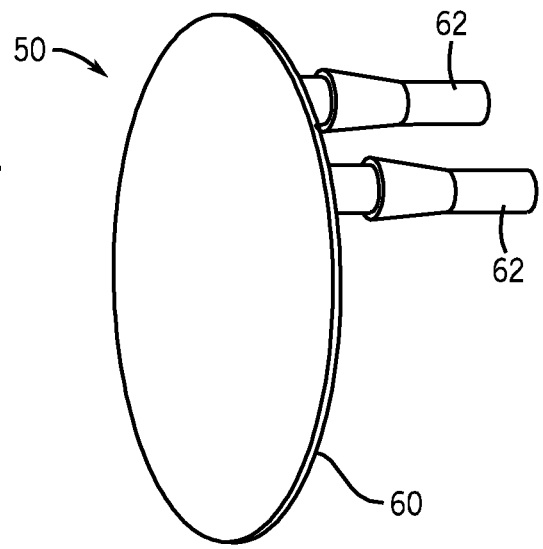
FIG. 4 is an isometric view illustrating a valve flap of the valve assembly of FIG. 3 in accordance with an embodiment.

Having described the operation of the flow sensor 18, some of the flow sensor 18 components will now be described in more detail. Referring to FIG. 4, the valve flap 50 of the flow sensor 18 (shown in FIG. 3) is shown in accordance with an embodiment. The valve flap 50 is preferably composed of material that can be repeatedly elastically deformed without failure such as, for example, an elastomer. The valve flap 50 includes a generally disc-shaped sealing portion 60 and one or more protrusions 62. The valve flap 50 will hereinafter be described as including two generally identical protrusions 62 that are collectively configured to resist valve flap rotation, however it should be appreciated that other quantities and configurations may be envisioned.

Figure 5:
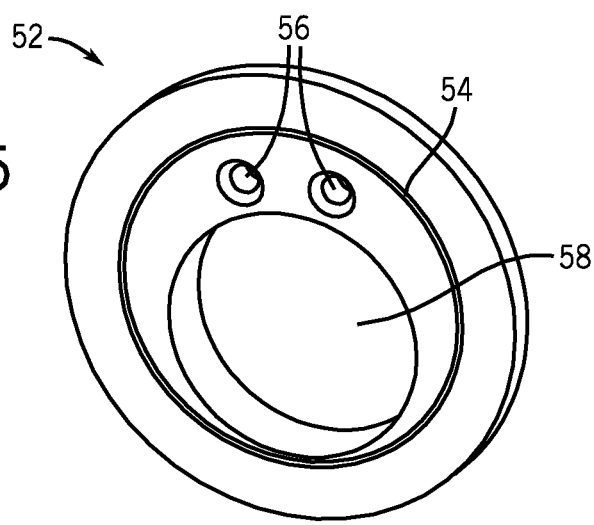
FIG. 5 is an isometric view illustrating a valve seat of the valve assembly of FIG. 3 in accordance with an embodiment.

Referring to FIG. 5, the valve seat 52 of the flow sensor 18 (shown in FIG. 3) is shown in accordance with an embodiment. The valve seat 52 is preferably composed of material that is inexpensive and easy to manufacture such as, for example, an injection moldable plastic. The valve seat 52 includes a seat ring 54 and a retention shoulder 55 (shown in FIG. 6). The valve seat 52 defines one or more attachment apertures 56, and a fluid flow aperture 58. The valve seat 52 will hereinafter be described as defining two generally identical attachment apertures 56 that are each configured to receive one of the protrusions 62 (shown in FIG. 4) in accordance with an embodiment, however it should be appreciated that other quantities and configurations may be envisioned.

FIG. 6 is an exploded sectional view showing the valve assembly 40 components prior to assembly in accordance with an embodiment. The valve flap 50 is depicted in alignment with the valve seat 52 such that when the components come together the outer periphery of the valve flap 50 engages and forms a seal with the seat ring 54 of the valve seat 52, and the protrusion 62 of the valve flap 50 extends at least partially through the attachment aperture 56 of the valve seat 52. FIG. 7 is a sectional view showing the valve assembly 40 in accordance with an embodiment.

Referring now to FIGS. 6 and 7, the protrusion 62 includes a terminal end portion 70, a reduced diameter portion 72, and a tapered portion 74 formed therebetween. The interface between the tapered portion 74 and the reduced diameter portion 72 defines a flange 76. The reduced diameter portion 72 will be described as having a length X, the terminal end portion 70 will be described as having a diameter V, and the tapered portion 74 will be defined as having a maximum diameter (i.e., as measured at the flange 76) of W as shown in FIG. 6. The tapered portion 74 is optional and may be implemented to facilitate assembly by simplifying the process of inserting the protrusion 62 through the attachment aperture 56.

The retention shoulder 55 of valve seat 52 defines a surface 80. The retention shoulder 55 circumscribes and thereby also defines the attachment aperture 56. The retention shoulder 55 will be described as having a width Y, and the attachment aperture 56 will be described as having a diameter Z as shown in FIG. 6.

When the valve flap 50 is assembled to the valve seat 52, the terminal end portion 70 of the protrusion 62 is inserted into the attachment aperture 56 of the valve seat 52. The diameter V of the terminal end portion 70 is preferably less than the diameter Z of the attachment aperture 56 to facilitate the insertion. The maximum diameter W of the tapered portion 74 is, however, preferably greater than the diameter Z of the attachment aperture 56 such that the tapered portion 74 must be forcibly passed through the attachment aperture 56 in a manner that compresses the protrusion 62. As previously described, the valve flap 50 may be comprised of an elastomeric material such that protrusion 62 elastically deforms during this compression and thereafter returns to its steady state configuration wherein the maximum diameter W of the tapered portion 74 exceeds that of the attachment aperture 56. After the tapered portion 74 is inserted into and passes completely through the attachment aperture 56, the flange 76 engages surface 80 of the retention shoulder 55 in order to secure the valve flap 50 to the valve seat 52.

According to one embodiment, the steady state length X of the reduced diameter portion 72 is less than the width Y of the retention shoulder 55 such that the reduced diameter portion 72 must be deformed or stretched during the assembly process described hereinabove. The process of deforming the protrusion 62 by stretching the reduced diameter portion 72 has the effect of generating a pre-load. This pre-load biases the valve flap 50 into engagement with the valve seat 52 such that the valve assembly 40 remains closed in the absence of an externally applied force. When an external force (e.g., from patient inspiration) is applied to the valve flap 50, the pre-load bias can be overcome and the valve opens. Advantageously, as soon as the external force is removed, the pre-load has the effect bringing the valve flap 50 back into engagement with the valve seat 52 such that the valve assembly 40 automatically closes.

The magnitude of the pre-load generated by stretching the reduced diameter portion 72 of the protrusion 62 is selectable such as, for example, by modifying the material composition; the degree to which the reduced diameter portion 74 is stretched; and/or the geometry of the protrusion 62. It is envisioned that the magnitude of the pre-load may be selected to be large enough to consistently close the valve assembly 40 in the absence of an external force, and small enough to be overcome by a typical patient's inspiration and/or expiration. In this manner, by appropriately selecting the magnitude of the pre-load, the valve assembly 40 can be automatically opened in response to a patient's inspiration and/or expiration, and thereafter the valve assembly 40 can automatically close.

While the aforementioned pre-load has been described in accordance with an embodiment as originating from the geometry and composition of the protrusions 62 (shown in FIG. 4), it should be appreciated that other embodiments may generate a similar pre-load from an alternate source. As an example, an elastomeric valve flap comprising a concave or otherwise curved sealing surface (not shown) could be forcibly brought into engagement with the valve seat 52 during the assembly process such that the geometry and composition of the entire valve flap generates the pre-load.

Figure 8:
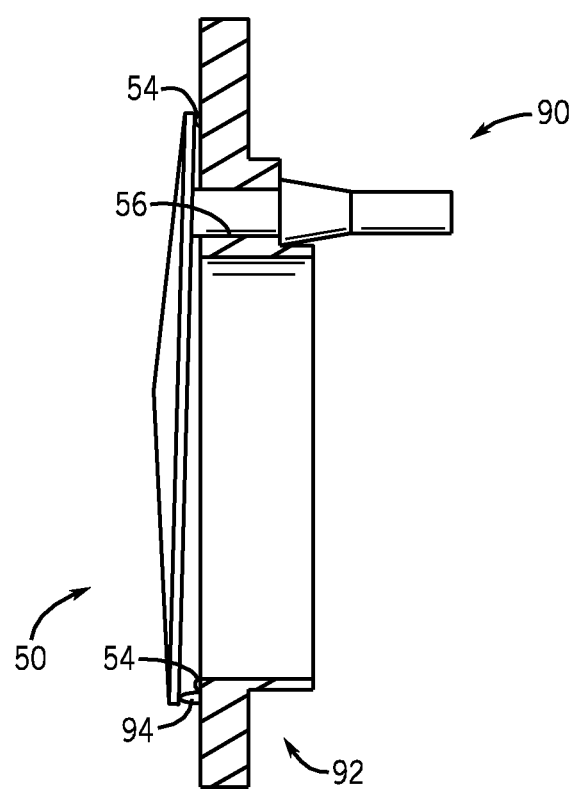
FIG. 8 is a sectional view illustrating a valve assembly in accordance with an embodiment.

Referring to FIG. 8, a sectional view shows the valve assembly 90 in accordance with an alternate embodiment. Common reference numbers will be used to identify similar components from previously described embodiments. The valve assembly 90 comprises the valve flap 50 and a valve seat 92.

The valve seat 92 includes pin 94 described in detail hereinafter, but is otherwise similar to the valve seat 52 (shown in FIG. 5). The pin 94 is a localized protrusion disposed in close proximity to the seat ring 54 at a radial position that is generally opposite the attachment aperture 56. The pin 94 protrudes or extends away from the remainder of the valve seat 92 in an axial direction by an amount that is slightly greater than that of the seat ring 54. When the valve assembly 90 is in its closed position, the pin 94 engages a discrete portion of the valve flap 50 and thereby maintains partial separation between the valve flap 50 and the seat ring 54. By maintaining partial separation between the valve flap 50 and the seat ring 54, surface tension attributable to moisture within the ventilator system 10 (shown in FIG. 1) is less likely to interfere with valve assembly 90 operation. More precisely, the surface tension attributable to moisture is less likely to generate adhesion between the valve flap 50 and the seat ring 54 such that the valve assembly 90 becomes stuck in the closed position.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

I claim:

1. A flow sensor for a medical ventilator system comprising:
    a valve assembly comprising:
        a valve seat comprising an attachment aperture, a seat ring, and a pin that extends from the valve seat past the seat ring; and
        a valve flap attached to the valve seat, the valve flap being composed of an elastomeric material and the valve flap comprising a protrusion configured to be received within the attachment aperture to retain the valve flap to the valve seat;
        wherein the elastomeric material of the protrusion generates a pre-load that biases the valve flap into engagement with the valve seat such that the valve assembly remains closed in the absence of an externally applied force and the valve flap engages the pin to limit engagement between the valve flap and the seat ring when the valve assembly is closed;
    a pressure transducer configured to measure a first pressure level at an upstream position relative to the valve assembly, and a second pressure level at a downstream position relative the valve assembly; and
    a processor connected to the pressure transducer, said processor configured to estimate the flow rate of a fluid passing through a medical ventilator system based on the first and second pressure levels.

2. The flow sensor of claim 1, wherein the pre-load generated by the elastomeric material of the valve flap is small enough to be overcome by a typical patient's inspiration and/or expiration.

3. The flow sensor of claim 1, wherein the valve flap comprises a pair of protrusions collectively configured to retain the valve flap to the valve seat, and to resist valve flap rotation.

4. The flow sensor of claim 1, wherein the valve flap protrusion comprises a tapered portion adapted to facilitate the insertion of the valve flap protrusion into the attachment aperture of the valve seat.

5. The flow sensor of claim 1, wherein the valve flap protrusion is elastically deformed during the process of attaching the valve flap to the valve seat, and wherein the elastic deformation of the valve flap protrusion biases the valve flap into engagement with the valve seat.

6. The flow sensor of claim 1, wherein the valve seat is configured to at least partially engage the valve flap when the valve assembly is closed.

7. The flow sensor of claim 1, further comprising a high-pressure tube and a low-pressure tube pneumatically coupled with the pressure transducer.

8. A medical ventilator system comprising:
a ventilator;
a breathing circuit pneumatically coupled with the ventilator and conveying a flow of medical gas;
a flow sensor pneumatically coupled with the breathing circuit, said flow sensor comprising:
a valve assembly comprising:
a valve seat including a snake generally perpendicular to the flow of medical gas, a seat ring, and a pin; and
a valve flap composed of an elastomeric material, said valve flap comprising a protrusion extending, away from the valve flap in an axial direction into the flow of medical gas, the protrusion deforms in the axial direction when connected to the valve seat to retain the valve flap to the valve seat;
wherein the elastic deformation of the valve flap protrusion in the axial direction generates a pre-load that biases the valve flap into engagement with the pin and the surface of the valve seat such that the valve assembly remains closed in the absence of a predetermined medical gas flow and the pin maintains a partial separation between portions of the valve flap and the valve seat;
a pressure transducer configured to measure a first pressure level at an upstream position relative to the valve assembly, and a second pressure level at a downstream position relative to the valve assembly; and
a processor connected to the pressure transducer, said processor configured to estimate the flow rate of the medical gas passing through the medical ventilator system based on the first and second pressure levels.

9. The medical ventilator system of claim 8, wherein the pre-load generated by the elastic deformation of the valve flap protrusion is small enough to be overcome by a typical patient's inspiration and/or expiration.

10. The medical ventilator system of claim 8, wherein the valve seat comprises an attachment aperture configured to receive the valve flap protrusion.

11. The medical ventilator system of claim 8, wherein the valve flap comprises a pair of protrusions collectively configured to retain the valve flap to the valve seat, and to resist valve flap rotation.

12. The medical ventilator system of claim 8, wherein the valve flap protrusion comprises a tapered portion adapted to facilitate the insertion of the valve flap protrusion into the attachment aperture of the valve seat.

13. The medical ventilator system of claim 8, wherein the seat ring is configured to partially engage the valve flap when the valve assembly is closed.

14. The medical ventilator system of claim 8, further comprising:
an attachment aperture in the valve seat configured to receive the protrusion, wherein the attachment aperture is of a first cross-sectional diameter and the protrusion comprises a flange portion of a second cross-sectional diameter, configured to engage the attachment aperture; and
wherein the second cross-sectional diameter is larger than the first cross-sectional diameter, and engagement of the first portion with the attachment aperture retains the valve flap to the valve seat.

15. The medical ventilator system of claim 14, wherein the attachment aperture is of a first length through the valve seat;
wherein the protrusion comprises a reduced diameter portion, of a second length, that extends between the valve flap and the flange portion of the protrusion; and
wherein the second length is shorter than the first length and engagement of the flange portion with the attachment aperture elastically deforms the reduced diameter portion in the axial direction, and the elastic deformation of the reduced diameter portion generates the pre-load on the valve flap.

16. A method for estimating a flow rate of a fluid passing through a medical ventilator system comprising:
providing a breathing circuit providing a valve assembly disposed at least partially within the breathing circuit comprising:
providing a valve flap composed of an elastomeric material;
assembling the valve flap to a valve seat such that the elastomeric material of a protrusion of the valve flap is elastically deformed in an axial direction during the assembly process, wherein the elastic deformation of the protrusion generates a pre-load that biases the valve flap into at least partial engagement with a seat ring of the valve seat perpendicular to the fluid and into at least partial engagement with a pin of the valve seat protruding past the seat ring such that the valve assembly remains closed in the absence of a predetermined medical gas flow while maintaining partial separation between the valve flap and the seat ring;
estimating with a first pressure transducer a first pressure level within the breathing circuit at art upstream position relative to the valve assembly;
estimating with a second pressure transducer a second pressure level within the breathing circuit at a downstream position relative to the valve assembly;
estimating with a processor a flow rate of a fluid passing through the breathing circuit based on the first and second pressure levels.

17. The method of claim 16, further comprising selecting the magnitude of the pre-load such that the valve assembly automatically opens in response to a patient's inspiration and/or expiration.

* * * * *